United States Patent
Plumptre et al.

(10) Patent No.: US 10,781,959 B2
(45) Date of Patent: Sep. 22, 2020

(54) CODED CARTRIDGE HOLDER AND FASTENER ENABLED BY CARTRIDGE SIZE

(71) Applicant: SANOFI-AVENTIS DEUTSCHLAND GMBH, Frankfurt am Main (DE)

(72) Inventors: David Plumptre, Worcestershire (GB); Christopher Nigel Langley, Warwickshire (GB); Richard James Vincent Avery, Gloucestershire (GB); Joseph Butler, Warwickshire (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 377 days.

(21) Appl. No.: 15/800,334

(22) Filed: Nov. 1, 2017

(65) Prior Publication Data

US 2018/0080592 A1 Mar. 22, 2018

Related U.S. Application Data

(63) Continuation of application No. 13/522,491, filed as application No. PCT/EP2011/050799 on Jan. 21, 2011, now Pat. No. 9,835,279.

(Continued)

(30) Foreign Application Priority Data

Apr. 23, 2010 (EP) ................................ 10160873

(51) Int. Cl.
*F16L 55/00* (2006.01)
*A61M 5/24* (2006.01)
*A61M 5/31* (2006.01)

(52) U.S. Cl.
CPC ............... *F16L 55/00* (2013.01); *A61M 5/24* (2013.01); *A61M 5/3135* (2013.01);
(Continued)

(58) Field of Classification Search
CPC ........ F16L 55/00; A61M 5/24; A61M 5/3135; A61M 2005/2407; A61M 2005/2488;
(Continued)

(56) References Cited

U.S. PATENT DOCUMENTS

| 533,575 | A | | 2/1895 | Wilkens |
| 3,811,441 | A | * | 5/1974 | Sarnoff ................... A61M 5/24 |
| | | | | 604/201 |

(Continued)

FOREIGN PATENT DOCUMENTS

| EP | 0485028 | 5/1992 |
| EP | 0937471 | 8/1999 |

(Continued)

OTHER PUBLICATIONS

European Examination Report for EP Application No. 11701084.3, dated Aug. 17, 2016.

(Continued)

*Primary Examiner* — Lauren P Farrar
(74) *Attorney, Agent, or Firm* — Fish & Richardson P.C.

(57) ABSTRACT

A coded cartridge holder for use with a drug delivery device is provided. The cartridge holder includes a fastener that becomes operative based in part on a length of a cartridge or a diameter of the cartridge. In one embodiment, the cartridge holder is coupled to the drug delivery device. The cartridge holder comprises a first blocking feature. The drug delivery device includes a cartridge detector comprising a second blocking feature. This feature may be a pin, for engagement with the first blocking feature of the cartridge holder when the cartridge acts on the cartridge detector. The cartridge holder may further include a fastening mechanism configured to fasten the cartridge holder to the drug delivery device only when the second blocking feature engages the first blocking feature.

15 Claims, 5 Drawing Sheets

Related U.S. Application Data

(60) Provisional application No. 61/297,611, filed on Jan. 22, 2010.

(52) U.S. Cl.
CPC .............. *A61M 2005/2407* (2013.01); *A61M 2005/2488* (2013.01); *A61M 2005/2492* (2013.01); *A61M 2205/276* (2013.01); *A61M 2205/6045* (2013.01); *Y10T 137/598* (2015.04)

(58) Field of Classification Search
CPC .... A61M 2005/2492; A61M 2005/276; A61M 2205/6045; Y10T 137/598
See application file for complete search history.

(56) References Cited

U.S. PATENT DOCUMENTS

| | | |
|---|---|---|
| 4,585,445 A | 4/1986 | Hadtke |
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0021718 A1* | 1/2007 | Burren ............ A61M 5/24 604/110 |
| 2009/0275916 A1* | 11/2009 | Harms ............ A61M 5/24 604/506 |
| 2011/0046566 A1 | 2/2011 | Elahi et al. |

FOREIGN PATENT DOCUMENTS

| | | |
|---|---|---|
| EP | 0937476 | 8/1999 |
| GB | 680224 | 10/1952 |
| JP | 3414760 | 6/2003 |
| WO | 97/30741 | 8/1997 |
| WO | 99/38554 | 8/1999 |
| WO | 01/10484 | 2/2001 |
| WO | 03/017915 | 3/2003 |
| WO | 2008/059063 | 5/2008 |
| WO | 2008/062025 | 5/2008 |
| WO | 2008/074897 | 6/2008 |

OTHER PUBLICATIONS

European Search Report for EP Application No. 10160873.5, dated Oct. 22, 2010.
International Preliminary Report on Patentability for Int. App. No. PCT/EP2011/050799, dated Aug. 2, 2012.
International Search Report for Int. App. No. PCT/EP2011/050799, completed Nov. 16, 2011.
Japanese Office Action for JP Application No. 2012-549365, dated Nov. 4, 2014.

\* cited by examiner

CODED CARTRIDGE HOLDER AND FASTENER ENABLED BY CARTRIDGE SIZE

CROSS REFERENCE TO RELATED APPLICATIONS

The present application is a continuation of U.S. patent application Ser. No. 13/522,491, filed Dec. 4, 2012, which is a U.S. National Phase Application pursuant to 35 U.S.C. § 371 of International Application No. PCT/EP2011/050799 filed Jan. 21, 2011, which claims priority to U.S. Provisional Patent Application No. 60/297,611 filed on Jan. 22, 2010 and also claims priority to European Patent Application No. 10160873.5 filed on Apr. 23, 2010. The entire disclosure contents of these applications are herewith incorporated by reference into the present application.

FIELD OF INVENTION

The present disclosure is generally directed to reservoirs, particularly reservoirs containing a medicament. More particularly, the present disclosure is generally directed to a coded cartridge holder and a fastener enabled by a cartridge intended for use with the cartridge holder, for example a cartridge having the correct size, so as to prevent unwanted reservoir cross use. As just one example, such medicament reservoirs may comprise an ampoule, a cartridge, a vial, or a pouch, and may be used with a medical delivery device. Exemplary medical delivery devices include, but are not limited to syringes, pen type syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge housing is disconnected from the drug delivery device and the empty cartridge is removed and replaced with a new cartridge. Most suppliers of such cartridges recommend that the user disposes of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long acting insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design a drug delivery device, for example an injection device, that only accepts or works with the dedication or coded features provided on or with the cartridge so as to prevent unwanted cartridge cross use. Similarly, there is also a general need for a dedicated cartridge that allows the medical delivery device to be used with only an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

The problem to be solved by the present invention is to provide a drug reservoir and a drug delivery system where the safety for the user is improved.

SUMMARY

For purposes of the present disclosure, a cartridge dimension, such as length or diameter, may indicate a particular drug or medicament. A cartridge holder may be coupled to (e.g., inserted into) a drug delivery device. If the cartridge or drug is correct for the device (i.e., the cartridge has the correct dimension), the cartridge holder may be properly secured, i.e., fastened to the drug delivery device. In particular, a fastening mechanism may be enabled or is allowed to function properly. The fastening mechanism may be enabled by the cartridge and, in particular, by a mechanical interaction of the cartridge with the cartridge holder or a part of the drug delivery device, to fasten the cartridge holder to the device. On the other hand, if the cartridge or drug is not correct for the drug delivery device (i.e., the cartridge has an incorrect dimension), the fastening mechanism may be disabled from functioning properly. Thereby, the cartridge holder cannot be properly secured to the device. Thus, this system ensures that the appropriate cartridge can only be used with the correct drug delivery device.

According to one aspect, a cartridge holder for use with a drug delivery device, for example a pen type drug delivery device is provided. The cartridge holder may comprise an inner bore being configured to receive a cartridge, for example a glass cartridge. The cartridge holder may further comprise a fastening mechanism configured to fasten the cartridge holder to the drug delivery device. The fastening mechanism may comprise a first fastener configured to engage with a second fastener of the drug delivery device for fastening the cartridge holder to the drug delivery device. As examples, the first fastener may comprise a pin, a tab or a groove. The second fastener may comprise a corresponding feature engageable with the first fastener. The fastening mechanism may comprise any means suitable for securely fastening the cartridge holder to the drug delivery device.

The fastening mechanism may be configured such that an elastic deformation of at least one of part of the drug delivery device and the cartridge holder by mechanical interaction with a cartridge accommodated in the cartridge holder enables fastening the cartridge holder to the drug delivery device. In particular, the fastening mechanism may be configured such that only if a cartridge intended for use with the drug delivery device and, in particular, a cartridge having the correct dimension, for example the correct length or diameter, is accommodated in the cartridge holder, fastening is enabled. Accordingly, a fastening of the cartridge holder to the drug delivery device may be disabled by a cartridge having an incorrect dimension, for example an incorrect length or diameter.

The cartridge holder may be configured such that an accommodated cartridge acts on the fastening mechanism of the cartridge holder. In particular, the cartridge may act on a part of the fastening mechanism and thereby elastically deform the part of the fastening mechanism. As an example, the cartridge may act with its proximal end on the fastening mechanism. The elastic deformation may result in the correct configuration of the fastening mechanism, and, in particular, of the first fastener such that an engagement of the first fastener with a corresponding second fastener of the device is enabled. As examples, the fastening mechanism may comprise an inwardly facing sprung arm or an elliptical ring comprising the first fastener. By a deformation of the sprung arm or the elliptical ring, the first fastener may be pushed radially outwards by a portion of a cartridge such that the fastener is in the correct position for engagement with a second fastener of the drug deliver device.

The cartridge holder may comprise a first blocking feature configured for engagement with a second blocking feature of the drug delivery device, if a correct cartridge is accommodated in the cartridge holder. As examples, the first blocking feature may comprise a notch or a pin. The second blocking feature may have a corresponding design. On an elastic deformation of a part of the drug delivery device the first blocking feature may be enabled to engage with the second blocking feature, thereby enabling a fastening of the cartridge holder to the drug delivery device. In particular, the drug delivery device may comprise a cartridge detector, wherein on elastic deformation of a part of the cartridge detector by a correct cartridge, fastening of the cartridge holder to the drug delivery device is enabled. Here, a proximal end of the cartridge may act on the cartridge detector. The cartridge detector may comprise a resilient member, for example a spring, which is elastically deformed by the cartridge. The cartridge detector may comprise the second blocking feature. By an elastic deformation of a part of the cartridge detector by a correct cartridge, the second blocking feature may get into a correct position, for example a correct axial position, to engage with the first blocking feature. If an incorrect cartridge is accommodated in the cartridge holder, the second blocking feature may not get into the correct position such that an engagement with the first blocking feature is disabled. In an alternative embodiment, the cartridge may deform a part of the cartridge holder to enable engagement of the first and second blocking feature.

According to a specific embodiment, a cartridge holder for use with a drug delivery device is provided. The cartridge holder comprises an inner bore being configured to receive a cartridge and a fastening mechanism configured to fasten the cartridge holder to the drug delivery device. The fastening mechanism is configured such that an elastic deformation of at least one of part of the drug delivery device and the cartridge holder by mechanical interaction with a cartridge accommodated in the cartridge holder enables fastening the cartridge holder to the drug delivery device.

According to a specific embodiment, a cartridge holder for use with a drug delivery device is provided. The cartridge holder comprises an inner bore being configured to receive a cartridge and a fastening mechanism enabled by a proximal end of the cartridge. The fastening mechanism comprises at least one inwardly facing sprung arm.

According to a further specific embodiment, a cartridge holder for use with a drug delivery device is provided. The cartridge holder comprises an inner bore being configured to receive a cartridge and a fastening mechanism enabled by a proximal end of the cartridge. In particular, the fastening mechanism may be enabled by a mechanical interaction of the proximal end of the cartridge and the fastening mechanism. The fastening mechanism may include an elliptical ring.

According to a further aspect, a drug delivery device for use with a cartridge holder is provided. The cartridge holder may accommodate a cartridge and may be secured to the drug delivery device. The drug delivery device may include an inner bore configured to receive the cartridge holder. The cartridge holder may have any of the structural or functional properties as described above. In particular, the cartridge holder may comprise a fastening mechanism. The cartridge holder may further comprise a first blocking feature. A cartridge detector may be located within an inner bore of the delivery device, and may include a second blocking feature for engagement with the first blocking feature when the cartridge acts on the cartridge detector. The drug delivery device may comprise a fastening mechanism configured to interact with a fastening mechanism of the cartridge holder to fasten the cartridge holder to the drug delivery device. Here, a fastening may only be enabled when the second blocking feature engages the first blocking feature.

According to a specific embodiment, a drug delivery device for use with a cartridge holder is provided. The cartridge holder may have any functional and structural properties as described in this disclosure. The cartridge holder accommodates a cartridge and is configured to be attached to the drug delivery device. The drug delivery device comprises a device fastening mechanism configured to interact with the fastening mechanism of the cartridge holder to fasten the cartridge holder to the drug delivery device when the cartridge holder accommodates a correct cartridge.

According to a specific embodiment a drug delivery device for use with a cartridge holder is provided. The cartridge holder accommodates a cartridge and is configured to attach to the drug delivery device. The drug delivery device comprises an inner bore being configured to receive the cartridge holder. The cartridge holder includes a first blocking feature. Furthermore, the drug delivery device includes a cartridge detector located within the inner bore including a second blocking feature for engagement with the first blocking feature when a portion of the cartridge acts on the cartridge detector.

According to a further aspect, a method for securing a cartridge holder into a drug delivery device is disclosed. The method comprises the steps of providing a cartridge holder including a cartridge, wherein the cartridge holder has a first blocking feature. The method further comprises providing a drug delivery device having a second blocking feature and coupling the cartridge holder to the drug delivery device so that a portion of the cartridge acts upon a cartridge detector located within the drug delivery device to align a first blocking feature with a second blocking feature. The first blocking feature may be a part of the cartridge holder and the second blocking feature may be a part of the drug delivery device. In particular, the second blocking feature may be a part of a cartridge detector as described above. The method may further comprise the step of rotating the cartridge holder so that the second blocking feature engages the first blocking feature. Here, a rotation may be only enabled, when the first blocking feature is aligned with the second blocking feature. By the rotation of the cartridge holder and the engagement of the first and second blocking feature, a fastening of the cartridge holder to the device may be enabled. The method may further comprise fastening the cartridge holder to the drug delivery device by a fastening mechanism.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1A:
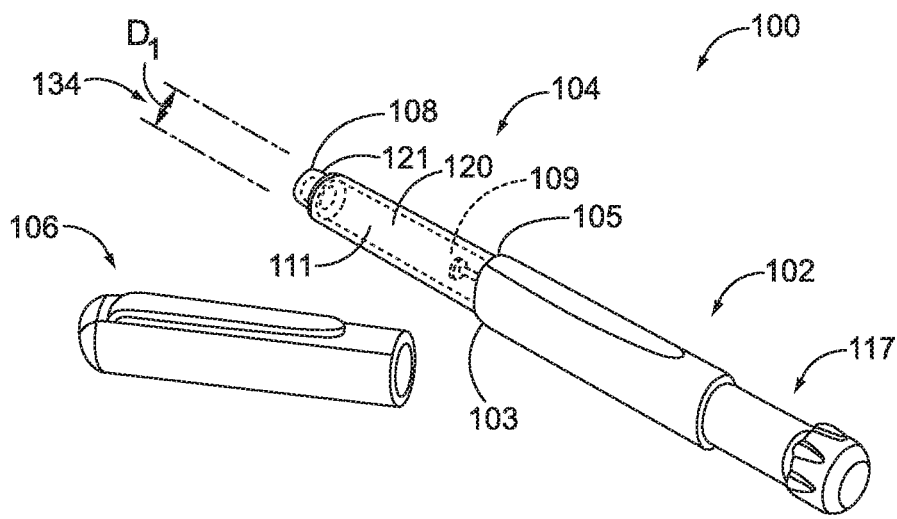
FIG. 1A illustrates an exemplary pen type drug delivery device.

Referring to FIG. 1A, there is shown a drug delivery device 100 in the form of a pen type syringe. The drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The pen type syringe may comprise a re-usable or a disposable pen type syringe. Where the syringe comprises a re-usable device, the cartridge holder 104 and the dose setting mechanism are removably coupled together. In a disposable device, they are permanently coupled together. In FIG. 1A, the dose setting mechanism 102 comprises a piston rod 109, such as a threaded piston rod that rotates when a dose is injected.

To inject a previously set dose, a double ended needle assembly (not shown) is attached to a distal end 108 of the cartridge holder 104. Preferably, the distal end 108 of the holder 104 comprises a thread 121 (or other suitable connecting mechanism such as a snap lock, snap fit, form fit, or bayonet lock mechanism) so that the needle assembly may be removably attached to the distal end 108 of the holder. When the drug delivery device 100 is not in use, the removable cap 106 can be releasably retained over the cartridge holder 104.

Figure 1B:
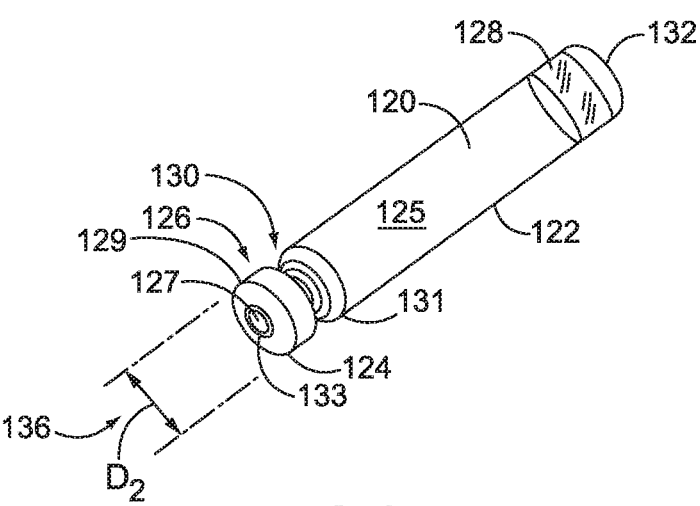
FIG. 1B illustrates an exemplary drug cartridge.

An inner cartridge cavity 111 defined by the cartridge holder 104 is dimensioned and configured to securely receive and retain a cartridge, such as glass cartridge 120. FIG. 1B illustrates a perspective view of the cartridge 120 that may be used with the drug delivery device 100 illustrated in FIG. 1A. Typically, the cartridge 120 is manufactured of glass and includes a generally tubular barrel 122 extending from a distal end 130 to a proximal end 132. The cartridge 120 may be inserted into an inner bore 101 of the drug delivery device 100.

At the distal end 130, the cartridge 120 includes a smaller diameter neck 126, wherein this neck 126 projects distally from the shoulder 131 of the barrel 122. Preferably, the smaller diameter neck 126 is provided with a large diameter annular bead 124 which extends circumferentially thereabout at the extreme distal end of the neck 126 and defines an opening 127. A pierceable seal or septum 133 is securely held across the opening 127 by a metallic sleeve or a ferrule.

Medicament 125 is pre-filled into the cartridge 120 and is retained within this cartridge 120, in part, by the pierceable seal 133, a ferrule, and a stopper 128. The stopper 128 is in sliding fluid-tight engagement with the inner tubular wall of the barrel 122. Axially directed forces acting upon the stopper 128 during dose injection or dose administration urge the medication 125 from the cartridge 120 though a double ended needle mounted onto the distal end 130 of the cartridge holder 104 and into the injection site. Such axially forces may be provided by the piston rod 109 working in unison with the dose setting member 102.

A portion of the cartridge holder 104 defining the cartridge holder cavity 111 is of substantially uniform diameter represented in FIG. 1A by $D_1$ 134. This diameter $D_1$ 134 is preferably slightly greater than the diameter $D_2$ 136 of the cartridge 120. The interior of the cartridge holder 104 includes an inwardly-extending annular portion or stop that is dimensioned to prevent the cartridge 120 from moving within the cartridge holder 104. In this manner, when the cartridge 120 is loaded into the cavity 111 of the cartridge holder 104 and the cartridge holder 104 is then connected to the dose setting member 102, the cartridge 120 will be securely held within the cartridge holder cavity 111. The cartridge holder 104 may also include a fastening mechanism for securing the cartridge holder 104 within the drug delivery device 100, which is described in more detail below.

A number of doses of a medicament 125 may be dispensed from the cartridge 120. Preferably, the cartridge 120 contains a type of medicament that must be administered often, such as one or more times a day. One such medicament is insulin.

The dose setting mechanism 102 comprises a dose setter 117 at the proximal end of the dose setting mechanism 102. In one preferred arrangement, the dose setter 117 is rotated to set a dose. To administer this set dose, the user attaches the needle assembly comprising a double ended needle on the distal end of the cartridge holder 104. In this manner, the needle assembly pierces the seal 133 of the cartridge 120 and is therefore in liquid communication with the medicament 125. The user pushes on the dose setter 117 to inject the set dose. The same dose setting and dose administration procedure is followed until the medicament 125 in the cartridge 120 is expended and then a new cartridge must be loaded in the drug delivery device 100. To exchange an empty cartridge 120, the user is called upon to remove the cartridge holder 104 from the dose setting mechanism 102.

Figure 2:
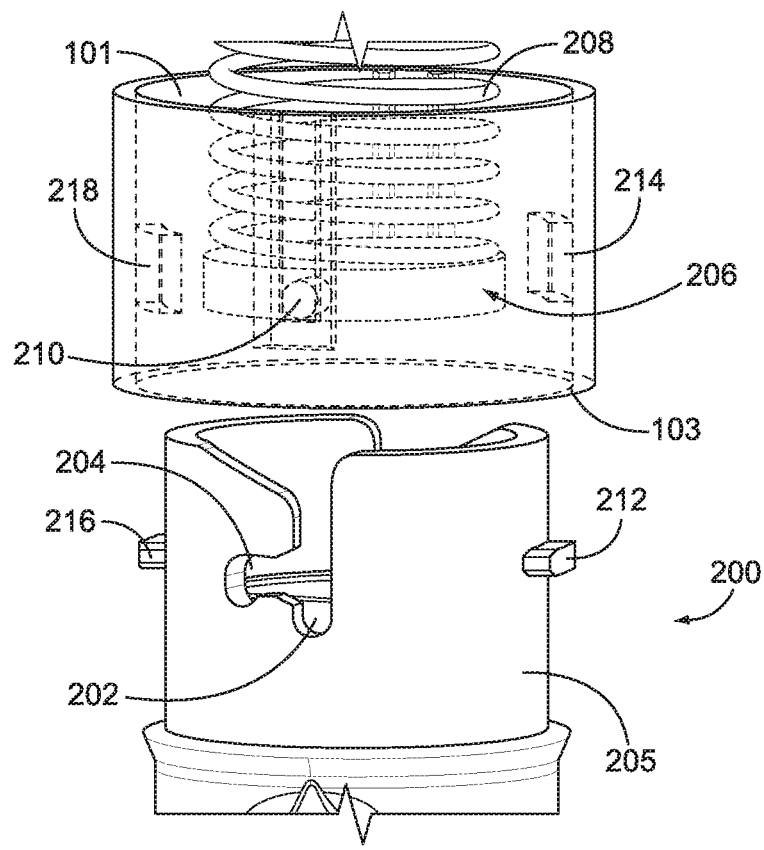
FIG. 2 illustrates a coded cartridge holder including a fastening mechanism enabled by cartridge size.

In accordance with exemplary embodiments, a cartridge holder such as cartridge holder 104 may be coded to a delivery device, so that given cartridge holders may only be connected with intended drug delivery devices and vice versa. FIG. 2 illustrates a first arrangement of a coded cartridge holder 200. This coded cartridge holder 200 may be connected to a drug delivery device, such as drug delivery device 100. For instance, the cartridge holder 200 may be attached to a drug delivery device that has a similarly coded portion. This similarly coded portion may be, for example, a locking mechanism and/or fastening mechanism that is enabled only by the correct length and/or diameter of the cartridge 200. The coded cartridge holder 200 is intended for use with a drug delivery device similar to the drug delivery device of FIG. 1A, but a preferred drug delivery device for use with the coded cartridge holder 200 would have a slightly modified inner cavity.

FIG. 2 illustrates a first arrangement of a coded cartridge holder 200 of the drug delivery device 100. In this arrangement, cartridge length indicates a particular drug or medicament. A cartridge, such as cartridge 120, of a particular length is inserted into the coded cartridge holder 200, which is then inserted into the drug delivery device 100. If the cartridge 120 or drug is correct for the device 100, the cartridge holder 200 may be properly secured to the drug delivery device 100 by a fastening mechanism, such as fasteners 212, 216. However, if the cartridge 120 or drug is not correct for the device 100, (e.g., the cartridge 120 is too short or too long or too wide), the fastening mechanism will not be enabled to function properly, and the cartridge holder 200 cannot be properly secured to the drug delivery device 100. Thus, this system ensures that the appropriate cartridge 120 or drug (i.e., the appropriately sized cartridge) can only be fastened to the correct delivery device 100.

The coded cartridge holder 200 may include a first blocking feature 202, 204. The first blocking feature 202, 204 may engage with a second blocking feature 210 to ensure that the correct length cartridge 120 and thus the correct drug or medicament is being used with the drug delivery device 100. The first blocking feature 202, 204 may include a slot 202 located on a proximal end 205 of the cartridge holder 200. The slot 202 may further include a notch 204 arranged perpendicular to the slot 202, as shown in FIG. 2. The notch 204 may retain the second blocking feature 210, located within an inner bore 101 of the drug delivery device 100, when the correct length cartridge 120 is inserted into the drug delivery device 100. The second blocking feature 210 may include a pin 210. The notch 204 allows the cartridge holder 200 to be rotated and positioned into place within the drug delivery device 100 when the pin 210 travels up through the slot 202.

It should be understood that although the slot 202 and notch 204 are shown on the cartridge holder 200, they could be located on the drug delivery device 100. Similarly, the pin 210 may be located on the cartridge holder 200. Alternatively, one or more slots 202 could be on the cartridge holder 200 and one ore more notches 204 on the drug delivery device 100.

Referring again to FIG. 2, the distal end 103 of the drug delivery device 100 may include a cartridge detector 206 located within its inner bore 101. The second blocking feature 210 may be located on the cartridge detector 206. The detector 206 may be a sprung plate 206. The sprung plate 206 may include a spring 208 or any other suitable biasing device. The sprung plate 206 is moveable along a longitudinal axis of the inner bore 101 of the drug delivery device 100. The sprung plate 206 may be actuated by a cartridge 120 when the correct length cartridge 120 is inserted into the cartridge holder 200. The sprung plate 206 may also bias the cartridge 120 against the cartridge holder 200 so as to improve dose accuracy.

The coded cartridge holder 200 may further include at least one fastening mechanism 212, 214. The fastening mechanism 212, 214 is enabled when the second blocking feature 210 engages the first blocking feature 202, 204, which indicates that the correct length cartridge 120 has been inserted into the drug delivery device 100. The fastening mechanism 212, 214 may be a bayonet fastening mechanism, for example. Alternatively, the fastening mechanism may be any suitable fastening mechanism, such as a snap lock, snap fit, form fit, etc. The fastening mechanism 212, 214 may include a first fastener 212, such as a pin 212, located near the proximal end 205 of the cartridge holder 200, and a second fastener 214, which may be a corresponding groove 214 located near the distal end 103 of the drug delivery device 100. In a preferred embodiment, a second fastening mechanism 216, 218 may be included on the cartridge holder 200 to more securely fasten the cartridge holder 104 to the drug delivery device 100. The second fastening mechanism 216, 218 may include a second pin 216 and a second corresponding groove 218.

Figure 3:
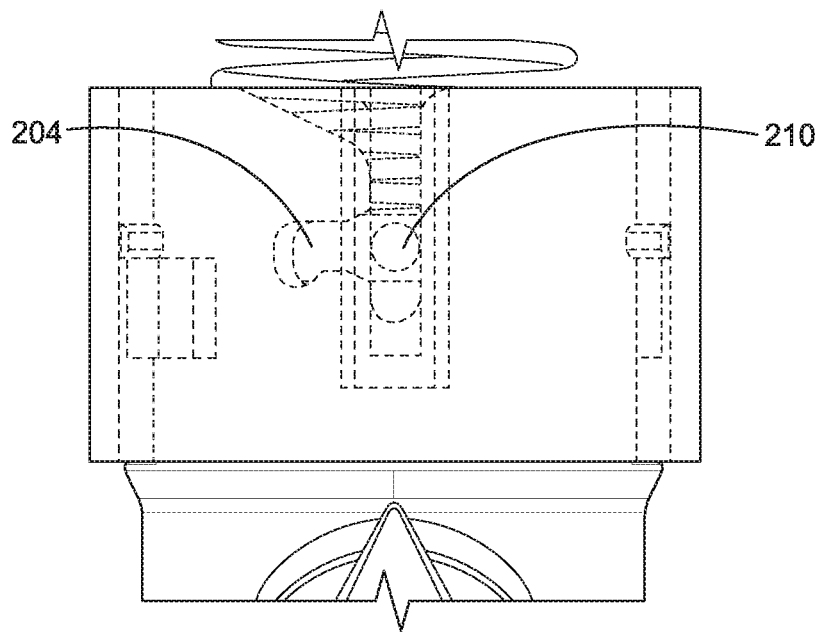
FIG. 3 illustrates a close-up view of the cartridge holder of FIG. 2 being inserted into the drug delivery device.
Figure 4:
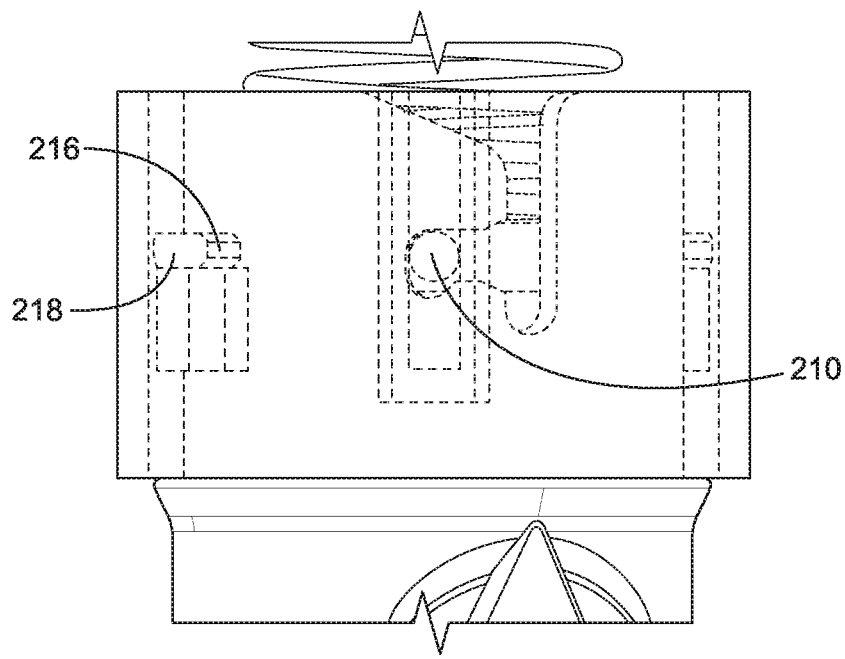
FIG. 4 illustrates a close-up view of a correct cartridge fastened within the drug delivery device of FIG. 2.
Figure 5:
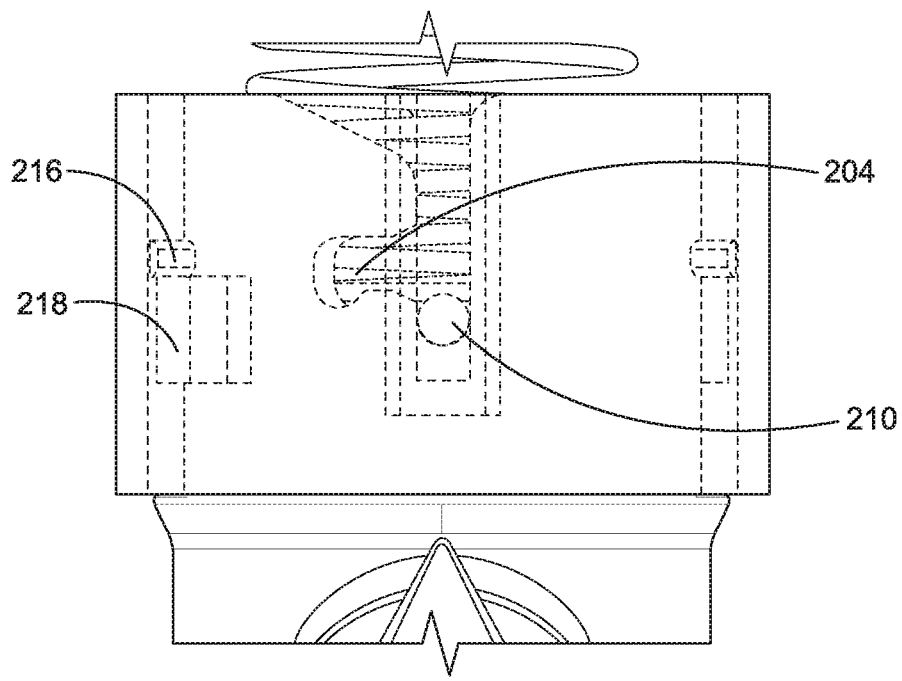
FIG. 5 illustrates a close-up view of an incorrect cartridge placed in the drug delivery device of FIG. 2.

In operation, as shown in FIGS. 3 and 4, when the cartridge holder 200 is first inserted into the drug delivery device 100, the proximal end of the cartridge 120 contacts the sprung plate 206 in the inner bore of the drug delivery device 100. This proximal end of the cartridge 120 pushes against the sprung plate 206 to move this plate 206 along the longitudinal axis of the drug delivery device 100. If the drug cartridge 120 has the correct length for this particular drug delivery device 100, the pin 210 on the sprung plate 206 will align with the slot 202 in the cartridge holder 104, and is moved until it is in line with the notch 204. The cartridge holder 200 may then be rotated so that the pin 210 slides along the notch 204. As the pin 210 slides along the notch 204, the pins 212, 216 of the fastening mechanisms 212, 214, 216, 218 also engage with the corresponding grooves 214, 218. The cartridge holder 200 is thus properly fastened to the drug delivery device 100. If the drug cartridge 120 is too short or too long and is therefore not the correct cartridge 120 for that particular drug delivery device 100, the pin 210 will not properly align with the notch 204. As such, the pins 212, 216 will not engage with the grooves 214, 218 on the drug delivery device 100. Thus, the cartridge holder 200 cannot be rotated or fastened to the drug delivery device 100, as shown in FIG. 5.

One advantage of the disclosed coded cartridge holder system is that it prevents assembly of cartridges that are either too short or too long for a given drug delivery device, thereby preventing the accidental intake of the wrong type of drug by a patient.

Figure 6:
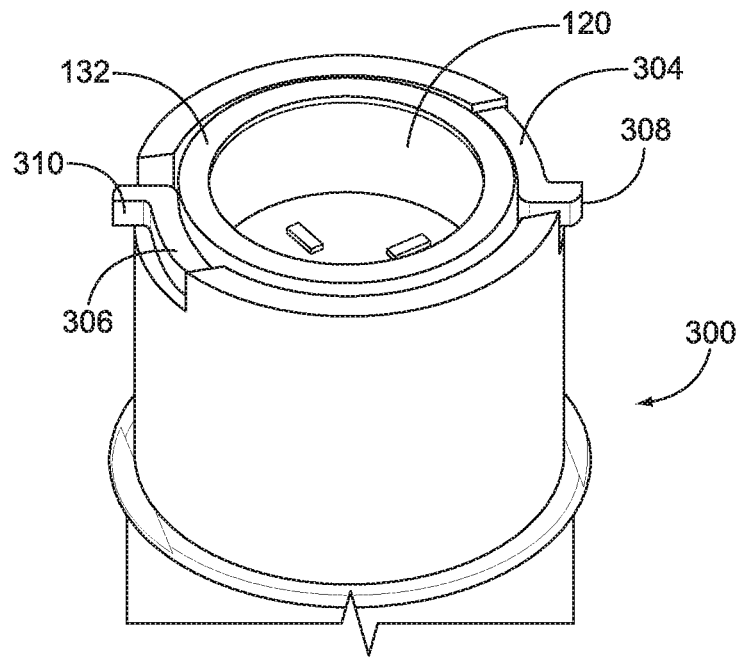
FIG. 6 illustrates another embodiment of a coded cartridge holder including a fastening mechanism enabled by cartridge size.
Figure 7:
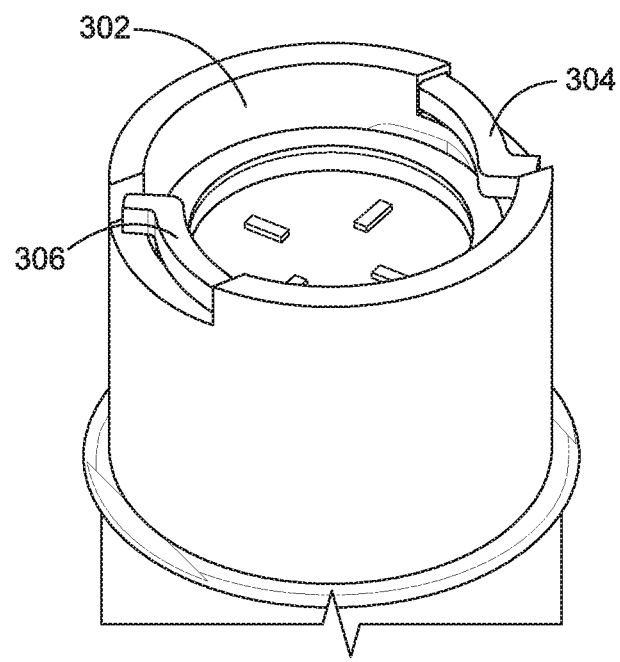
FIG. 7 illustrates a close-up view of an incorrect cartridge placed in the drug delivery device of FIG. 6.

FIGS. 6 and 7 illustrate a second arrangement of a coded cartridge holder 300 for use with a cartridge, such as the cartridge 120 illustrated in FIG. 1B, that may be used with a pen type drug delivery device, such as the drug delivery device 100 illustrated in FIG. 1A. Similar to the coded cartridge holder 200 illustrated in FIGS. 2-5, this cartridge configuration comprises a cartridge 120 inserted into a cartridge holder 300, similar to cartridge holder 104 illustrated in FIG. 1A, the size of the cartridge 120 indicating a particular drug.

The coded cartridge holder 300 includes an inner bore 302 being configured to receive a cartridge 120. The cartridge holder 300 may further include a fastening mechanism 304, 306 which interacts with a proximal end 132 of the cartridge 120. In this way, when a correctly dimensioned cartridge 120 is placed in the cartridge holder 300, it may be fastened by the fastening mechanism 304. Therefore, if an incorrectly dimensioned cartridge 120 is inserted into the cartridge holder 300, the holder 300 can not be connected to the drug delivery device 100.

The fastening mechanism 304, 306 may include at least one inwardly sprung arm 304. In a preferred embodiment, which is shown in FIG. 6, the fastening mechanism 304, 306 includes two inwardly sprung arms 304, 306. Although the embodiment shows two arms 304, 306, any number of arms may be used. The inwardly sprung arms 304, 306 may be molded as part of the cartridge holder 300, or they may be a separate component. The inwardly sprung arms 304, 306 may each include an outwardly projecting pin 308, 310.

As well as coding the drug by cartridge length, this embodiment also allows coding by cartridge diameter. For example, if the diameter of the cartridge 120 is too large, the cartridge will not fit in the holder 300. Further, if the diameter of the cartridge 120 is too small, the fastening mechanism 304, 306 would not be enabled and thus could not secure the cartridge holder to the drug delivery device 100.

In operation, when the cartridge 120 is inserted into the cartridge holder 300, the inwardly sprung arms 304, 306 are pushed outwards by the proximal end 132 of the cartridge 120 so that they may act as fastening features. The outwardly projecting pins 308, 310 may then mate with corresponding grooves on the drug delivery device 100, such as grooves 214, 218 shown in FIG. 2, to securely fasten the cartridge holder 300 to the drug delivery device 100.

If the cartridge 120 is too long, it may interfere with the drug delivery device 100 during fastening. If the cartridge 120 is too short, as shown in FIG. 7, the outwardly projecting pins 308, 310 of the inwardly sprung arms 304, 306 will not be exposed and therefore will not be able to mate with the corresponding grooves, such as grooves 214, 218 on the drug delivery device 100.

To ensure adequate strength, the inwardly sprung arms 304, 306 may be flexible in the radial direction, but relatively stiff in an axial direction. Alternatively, the inwardly sprung arms may be supported in an axial direction.

It should be understood that any suitable fastening mechanism can be used to secure the cartridge holder 300 to the drug delivery device 100, for example a thread, a pin following a groove or other bayonet, or snap fit.

In one embodiment, slots (not shown) may be formed in the cartridge holder 300 to allow access for removing a cartridge 120 (e.g., an incorrect short cartridge 120). Alternatively, a separate removal tool could be supplied with the drug delivery device 100.

One advantage of such a coded cartridge arrangement is that it prevents use of cartridges 120 that are either too short or too long for a particular drug delivery device, or where the cartridge diameter is too large or too small, thereby preventing the accidental intake of the wrong type of drug by a patient.

Figure 8:
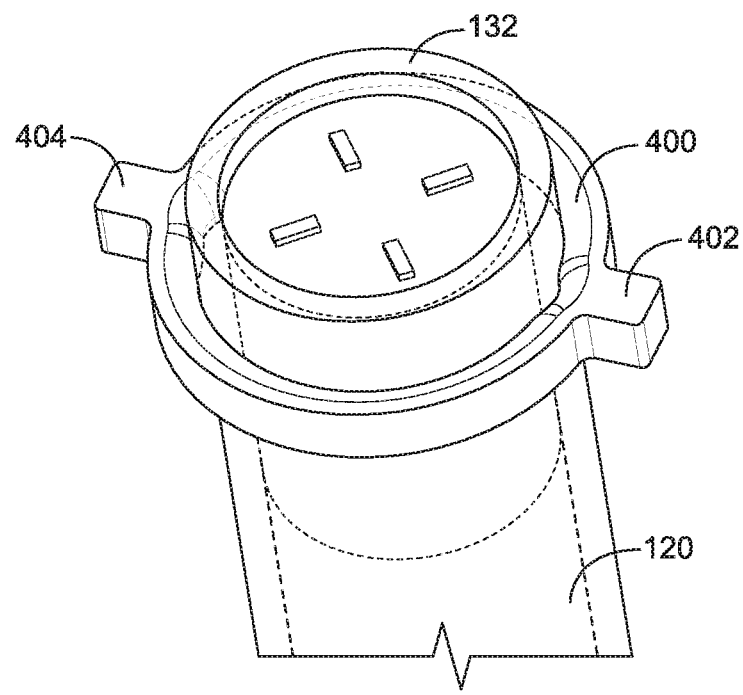
FIG. 8 illustrates yet another embodiment of a coded cartridge holder including a fastening mechanism enabled by cartridge size.
Figure 9:
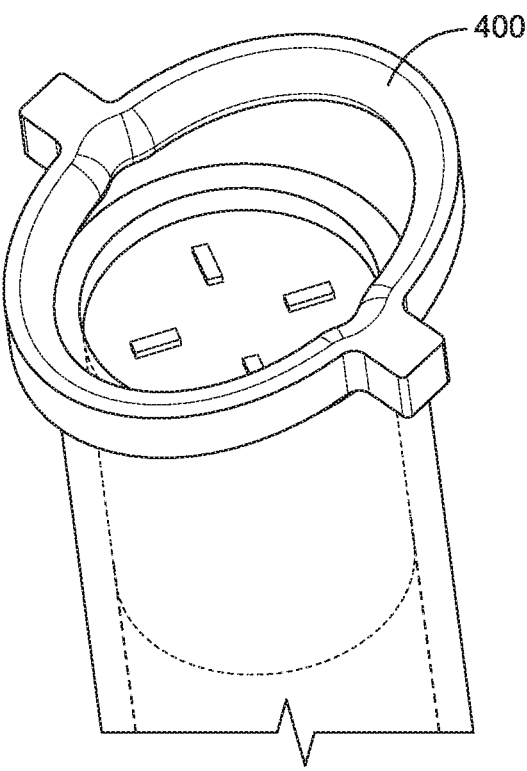
FIG. 9 illustrates a close-up view of an incorrect cartridge placed in the drug delivery device of FIG. 8.

FIGS. 8 and 9 illustrate a yet another arrangement of a coded cartridge holder, similar to cartridge holder 104, for use with a cartridge 120 that may be used with a drug delivery device, such as the pen type drug delivery device 100 illustrated in FIG. 1A. In this embodiment, an elliptical ring 400 may be attached into the cartridge holder (not shown) to act as the fastening mechanism for fastening the cartridge holder to the drug delivery device 100. The elliptical ring 400 may include one or more outwardly protruding tabs 402, 404. These tabs 402, 404 may engage with corresponding grooves, such as grooves 214, 218 as shown in FIG. 2, on the drug delivery device 100. It should be understood that any suitable fastening mechanism can be used to secure the cartridge holder to the drug delivery device 100 instead of the protruding tabs, for example a thread, a pin following a groove or other bayonet, or snap fit.

In operation, during the insertion of a correct cartridge into a cartridge holder, such as cartridge 120 into cartridge holder 104 illustrated in FIGS. 1A and 1B, the cartridge forces the elliptical ring 400 into a circular shape, thereby allowing the fastening mechanism, protruding tabs 402, 404, to protrude outwardly as shown in FIG. 8. The protruding tabs 402, 404 may then engage with corresponding grooves, such as grooves 214, 218 as shown in FIG. 2, on the drug delivery device 100 to securely fasten the cartridge 120 and cartridge holder 104 to the drug delivery device 100.

As shown in FIG. 9, if the cartridge 120 is incorrect for the drug delivery device 100, (e.g., the cartridge 120 is too short), the elliptical ring 400 will not be forced into a circular shape, and the protruding tabs 402, 404 will not engage with the corresponding grooves. To remove an incorrect cartridge 120, such as a cartridge 120 that is too short, the user may compress the ellipse on its major axis.

The disclosed coding system results in a number of advantages. For example, the disclosed coded cartridge holder arrangements assist a user to distinguish between medicaments, thereby helping to ensure that a delivery device can only be used with a medicament for which the device is intended.

The disclosed coded cartridge holder also prevents a user from completing one or more of the following actions: fully inserting the cartridge into an incorrect cartridge holder or attaching the cartridge and/or cartridge holder onto an incorrect dose setting mechanism.

The disclosed coded cartridge holder also results in a low cost coding mechanism since the disclosed cartridge holders do not require a large number of parts and can be manufactured in a cost effective manner. Moreover, there are quite a large number of different cartridge holder coding configurations between the cartridge holder and the drug delivery device that may be used. Consequently, with the disclosed coding schemes, a large number of medicaments can be distinguished from one another. In addition, with the disclosed coding schemes, if a user attempts to load an incorrect cartridge into a cartridge holder designed for a different cartridge, the user will be alerted at an early stage of the drug delivery device assembly process.

In addition, the disclosed system can be used to prevent errors during manufacturing, when inserting cartridges into disposable cartridge holders or disposable devices. With an incorrect drug (and hence incorrectly coded cartridge holder), the user is alerted at an early stage of the assembly process.

Exemplary embodiments of the present invention have been described. Those skilled in the art will understand, however, that changes and modifications may be made to these arrangements without departing from the true scope and spirit of the present invention, which is defined by the claims.

The invention claimed is:

1. A cartridge holder for use with a drug delivery device, the cartridge holder comprising:
   an inner bore being configured to receive a cartridge, the cartridge comprising a barrel and a stopper in sliding fluid-tight engagement with the barrel; and
   a fastening mechanism configured to fasten the cartridge holder to the drug delivery device,
   wherein the drug delivery device comprises:
      a dose setting mechanism comprising a piston rod to engage with the stopper of the cartridge; and
      a cartridge detector configured for mechanical interaction with the cartridge accommodated in the cartridge holder, wherein the fastening mechanism is configured such that only when a cartridge having a correct length or diameter is received in the inner bore, mechanical interaction between the cartridge detector and the cartridge having the correct length or diameter enables fastening of the cartridge holder to the dose setting mechanism.

2. The cartridge holder of claim 1, configured such that a fastening of the cartridge holder to the dose setting mechanism is disabled by a cartridge having at least one of an incorrect length or diameter.

3. The cartridge holder of claim 1, further comprising:
   a first blocking feature configured for engagement with a second blocking feature of the dose setting mechanism if the cartridge having the correct length or diameter is accommodated in the cartridge holder, and configured such that on a movement of a part of the cartridge detector along a longitudinal axis the first blocking feature is enabled to engage with the second blocking feature, thereby enabling a fastening of the cartridge holder to the dose setting mechanism.

4. The cartridge holder of claim 3, wherein the fastening of the cartridge holder to the dose setting mechanism is enabled by a cartridge-induced movement of the part of the cartridge detector along the longitudinal axis.

5. The cartridge holder according to claim 3, wherein the first blocking feature includes a pin or a slot located on a proximal end of the cartridge holder and being configured to engage with a correspondingly shaped slot or pin of the second blocking feature located on a distal end of the dose setting mechanism.

6. The cartridge holder according to claim 5, wherein the slot includes a notch arranged perpendicular to the slot and wherein the notch is configured to retain the pin when the cartridge having the correct length or diameter is inserted into the inner bore of the cartridge holder.

7. The cartridge holder according to claim 6, wherein the notch allows the cartridge holder to be rotated relative to the dose setting mechanism and positioned into place within the dose setting mechanism when the pin travels up through the slot.

8. The cartridge holder of claim 1, the fastening mechanism comprising:
   a first fastener configured to mechanically engage with a second fastener of the dose setting mechanism for fastening the cartridge holder to the dose setting mechanism.

9. The cartridge holder of claim 8, wherein the first fastener of the fastening mechanism comprises at least one of a pin, a tab, or a groove located near a proximal end of the cartridge holder.

10. The cartridge holder of claim 8, wherein the second fastener of the dose setting mechanism comprises at least one of a pin, a tab, or a groove located near a distal end of the dose setting mechanism, and wherein the first fastener of the fastening mechanism corresponds to the second fastener of the dose setting mechanism.

11. The cartridge holder of claim 8, wherein, if the cartridge having the correct length or diameter is accommodated in the cartridge holder, the mechanical interaction between the cartridge detector and the cartridge having the correct length or diameter results in a correct configuration of at least one of the first fastener or the second fastener such that an engagement of the first fastener with a corresponding second fastener of the dose setting mechanism is enabled.

12. A drug delivery device for use with a cartridge holder comprising an inner bore being configured to receive a cartridge, the cartridge comprising a barrel and a stopper in sliding fluid-tight engagement with the barrel, and a fastening mechanism configured to fasten the cartridge holder to the drug delivery device, the drug delivery device comprising:
   a dose setting mechanism comprising a piston rod to engage with a stopper of the cartridge and configured to interact with the fastening mechanism of the cartridge holder to fasten the cartridge holder to the drug delivery device when the cartridge holder accommodates a cartridge having a correct length or diameter; and
   a cartridge detector for mechanical interaction with the cartridge having the correct length or diameter, wherein the cartridge detector is configured such that fastening of the cartridge holder to the dose setting mechanism is enabled only by a mechanical interaction of the cartridge having the correct length or diameter with a part of the cartridge detector.

13. The drug delivery device of claim 12, wherein the cartridge detector comprises a second blocking feature for engagement with a first blocking feature of the cartridge holder, wherein a fastening of the cartridge holder to the dose setting mechanism by the fastening mechanism is enabled by an engagement of the first blocking feature of the cartridge holder with the second blocking feature of the cartridge detector.

14. A method for fastening a cartridge holder to a drug delivery device, the method comprising:
   providing a set of the cartridge holder and the drug delivery device, wherein
      the cartridge holder comprises:
         an inner bore being configured to receive a cartridge,
         a fastening mechanism configured to fasten the cartridge holder to the drug delivery device, and a first blocking feature, and
  the drug delivery device comprises:
    a cartridge detector configured for mechanical interaction with the cartridge accommodated in the cartridge holder, the cartridge detector comprising a second blocking feature, and
    a device fastening mechanism configured to interact with the fastening mechanism of the cartridge holder to fasten the cartridge holder to the drug delivery device when the cartridge holder accommodates a correct cartridge; and
  coupling the cartridge holder to the drug delivery device so that a portion of the correct cartridge acts upon the cartridge detector located within the drug delivery device to align the first blocking feature of the cartridge holder with the second blocking feature of the cartridge detector to thereby enable interaction of the fastening mechanism of the cartridge holder with the device fastening mechanism of the drug delivery device for fastening the cartridge holder to the drug delivery device.

15. The method of claim 14 further comprising:
  rotating the cartridge holder so that the second blocking feature engages the first blocking feature of the cartridge holder, wherein a fastening of the cartridge holder to the drug delivery device is enabled.

\* \* \* \* \*

UNITED STATES PATENT AND TRADEMARK OFFICE
CERTIFICATE OF CORRECTION

PATENT NO. : 10,781,959 B2  
APPLICATION NO. : 15/800334  
DATED : September 22, 2020  
INVENTOR(S) : Plumptre et al.

It is certified that error appears in the above-identified patent and that said Letters Patent is hereby corrected as shown below:

In the Specification

In Column 1, Line 12, delete "60/297,611" and insert -- 61/297,611 --

In the Claims

In Column 11, Line 66, Claim 6, delete "slot and" and insert -- slot, and --

Signed and Sealed this  
Twenty-ninth Day of December, 2020

Andrei Iancu  
*Director of the United States Patent and Trademark Office*